United States Patent [19]

Klein et al.

[11] Patent Number: 5,032,151
[45] Date of Patent: Jul. 16, 1991

[54] SYSTEM AND METHOD FOR AUTOMATED COOL ON-COLUMN INJECTION WITH COLUMN DIAMETERS LESS THAN 530 μM

[75] Inventors: Kenneth J. Klein; Wei J. Song, both of Wilmington, Del.; Ismael Rodriguez, Media; Richard J. Phillips, Landenberg, both of Pa.

[73] Assignee: Hewlett-Packard Company, Palo Alto, Calif.

[21] Appl. No.: 466,181

[22] Filed: Jan. 17, 1990

[51] Int. Cl.$^5$ .............................................. B01D 15/08
[52] U.S. Cl. .......................................... 55/20; 55/67; 55/269; 55/386
[58] Field of Search ...................... 55/67, 197, 386, 20, 55/267-269

[56] References Cited

U.S. PATENT DOCUMENTS

| | | | |
|---|---|---|---|
| 4,035,168 | 7/1977 | Jennings | 55/197 X |
| 4,181,613 | 1/1980 | Welsh et al. | 55/197 X |
| 4,269,608 | 5/1981 | Sisti et al. | 55/67 |
| 4,422,860 | 12/1983 | Feinstein | 55/67 |
| 4,440,550 | 4/1984 | Jenkins et al. | 55/197 X |
| 4,559,063 | 12/1985 | Munari et al. | 55/197 X |
| 4,615,226 | 10/1986 | DiNuzzo et al. | 73/864.87 |
| 4,704,141 | 11/1987 | Krebber | 55/197 |
| 4,732,581 | 3/1988 | Cheh et al. | 55/197 X |

FOREIGN PATENT DOCUMENTS

| | | | |
|---|---|---|---|
| 60-095348 | 5/1985 | Japan | 55/67 |
| 62-082353 | 4/1987 | Japan | 55/67 |
| 62-083660 | 4/1987 | Japan | 55/67 |

OTHER PUBLICATIONS

Schomburg, G., et al., Sampling Techniques In Capillary Gas Chromatography, Journal of Chromatography, 142 (1977), Amsterdam, pp. 87–102.

Grob, K., et al., On–Column Injection Onto Glass Capillary Columns, Journal of Chromatography, 151 (1978), Amsterdam, pp. 311–320.

Primary Examiner—Robert Spitzer
Attorney, Agent, or Firm—Richard F. Schuette

[57] ABSTRACT

A system and method are shown for performing cool, on-column sample injection into a chromatographic device having a capillary column which injection is achieved through the use of a syringe having a needle. The column diameter is minimized by the provision of an inlet assembly connected to the inlet end of the column, a sealing member disposed in the inlet assembly, for forming a fluid tight seal in the inlet end when the sample is injected onto the column to prevent the sample from escaping and for reducing the effective length of the needle at the point of insertion of the needle into the column and a guide member for reducing the effective length and for supporting the needle during insertion into the column. A temperature controller for controlling the temperature of the column in the region where the sample is injected is also disclosed. The sealing member is shown to include an elastomeric member and further the system includes a mechanism for continuously cooling the elastomeric member. The elastomeric member is shown to include a septum having a bore formed therein for passage of the needle therethrough. A new sample vial closure is also shown for use in the system, which closure applies only a minimal axial force on the needle. In such a system and method the need for a long syringe is obviated. The column inner diameter can be minimized by the system and method which permits the needle of the syringe to having a minimum outer circumference.

22 Claims, 4 Drawing Sheets

SYSTEM AND METHOD FOR AUTOMATED COOL ON-COLUMN INJECTION WITH COLUMN DIAMETERS LESS THAN 530 μM

FIELD OF THE INVENTION

The present invention relates to an advancement in the art of chromatography and, more particularly, to a chromatographic system capable of automated cool, on-column injection.

BACKGROUND OF THE INVENTION

In analytical chemistry, liquid and gas chromatography techniques have become important tools in the identification of chemical sample components. The basic principle underlying all chromatographic techniques is the separation of a sample chemical mixture into individual components by transporting the mixture in a moving fluid through a porous retentive media. The moving fluid is referred to as the mobile phase and the retentive media has been referred to as the stationary phase. One of the differences between liquid and gas chromatography is that the mobile phase is either a liquid or a gas, respectively.

In the analysis of a sample compound using a gas chromatograph, typically, a supply of inert carrier gas (mobile phase) is continually passed as a stream through a heated column containing porous sorptive media (stationary phase). In the past, chromatographic systems have incorporated columns formed as hollow capillary tubes having an inner diameter in the range of few hundred microns. In such systems, a sample of the subject mixture is injected into the mobile phase stream and passed through the capillary column, which column is typically positioned within an oven. As the subject mixture passes through the capillary column, it separates into its various components. Separation is due primarily to differences in the volatility characteristics of each sample component with respect to the temperature in the column. Column temperature is primarily regulated by oven temperature. A detector, positioned at the outlet end of the capillary column, detects each of the separated components as they exit the column.

Column efficiency (typically referred to in terms of theoretical plates) of capillary columns is dependent on both column length and width. A column having a larger inner diameter must be longer than a column having a smaller inner diameter in order to achieve comparable efficiency. As will be appreciated greater column length results in longer analysis times which can effect sensitivity. However, shorter columns with relatively narrower column inner diameters have, until the present invention, been limited in relation to the techniques available for sample injection. Consequently, certain prior gas chromatographic analyses have been a compromise between sensitivity and efficiency in relation to the column and injection technique utilized.

Moreover, it has been found for the analysis of particular compounds that the technique used to inject the sample compound and carrier gas into the column can have an effect on the qualitative and quantitative precision of the chromatographic analysis. So-called split and splitless injection techniques have been developed for the injection of a sample compound. Split injection techniques are used when it is desired to inject only a portion of the sample compound into the column, for example, when a sample containing high volume concentrations such as an undiluted material is to be analyzed. Splitless injection is used when it is desired to inject the whole sample, i.e., for trace analysis. The problems with both split and splitless techniques are irreproducibility and molecular weight discrimination which can occur in the sample vaporization step.

In Schomburg, G., et al., Sampling Techniques In Capillary Gas Chromatography, Journal of Chromatography, 142 (1977), Amsterdam, pps. 87–102 various GC injection or sampling techniques are studied and compared, including split and splitless injection. It is emphasized that technical difficulties involved in GC sampling are increased when quantitative analyses of trace components in complex mixtures are desired. It was observed that for optimal quantitative and qualitative analysis of complex mixtures, split and splitless techniques proved undesirable. It was concluded that through the use of on-column or direct sample introduction, improvements could be attained in both quantitative and qualitative analysis.

An on-column injection technique results in the sample compound being injected directly onto the column. Such direct injection can, however, result in the loss of volatile components which after rapid vaporization could be ejected from the inlet end of the column due to the pressure created by the injection. One solution to the ejection problem was the development of the cool, on-column injection technique.

In Grob, K., et al., On-Column Injection Onto Glass Capillary Columns, Journal of Chromatography, 151 (1978), Amsterdam, pps. 311–320, on-column injection is discussed in relation to precision and accuracy of qualitative analysis. An on-column injection apparatus is described as including a long narrow needle which is inserted into the column a preferred distance such that the needle tip lies approximately 10 mm within the oven. It is suggested that by removing the input septum, the precision of the analysis will be improved. In prior techniques, the input septum served to seal the inlet and the needle was required to pierce the septum in order to access the column. Grob et al. suggests cooling the injector assembly thereby establishing the cool on-column sample injection technique. In cool on-column sample injection the column in the region of the injection is cooled in relation to the boiling point of the sample in question in order to prevent vaporization and subsequent ejection of components from the column. In such an injection technique, any sample which is flushed from the oven back to the injector is deposited in the injector.

As used herein, quantitative precision refers to the relative standard deviation of the percent area count. Qualitative precision refers to the relative standard deviation of the retention time period.

U.S. Pat. No. 4,269,608 - Sisti et al. discloses an inlet system which provides a cooling gas stream for such a cool on-column injection technique. In Sisti the inlet apparatus is shown, in one embodiment, to have a coil which is said to be capable of drawing heat from, i.e. cooling, the inlet by passing a fluid at a suitable temperature therethrough. However, the disclosed design necessitates the use of long slender syringe needles to ensure that the needle tip is well within the oven region for deposit of liquid sample inside the capillary column. This necessity for long needles has inhibited an otherwise well accepted inlet design from ever being easily or robustly automatable.

In sum, it will be understood from the above that for certain analyses narrow capillary columns and cool on-column injection techniques are preferred. Such a combination, however, will require syringes having needles which are narrower than the column and as shown by Grob et al. are of sufficient length to extend at least 10 mm into the oven. Unfortunately, the combination of needle length and small diameter heretofore has resulted in undesirable bending and buckling, causing system failure. Such phenomena can be predicted in relation to the Euler Formula:

$$\frac{P_{CR}}{A} = \frac{\pi^2 E}{(L/R)^2}$$

where:
$P_{cr}$ = Critical Load
A = Cross-Sectional Area
L = Effective Length
R = Radius of Gyration
E = Modulus of Elasticity and
for $L/R > 150$.

One attempt to reduce column diameter and yet allow the use of wider diameter needles has been the development and use of so-called butt connectors. A butt connector can be used to join for example a 530 μm diameter pre-column with a 320 μm diameter analytical column. Unfortunately, the use of butt connectors can result in sacrifice of both efficiency, precision and ease of use.

It will be noted that one advantage of split and splitless techniques is that they can be readily automated. The automation of these techniques, particularly split injection, has significantly improved the precision and non-discrimination of chromatographic analysis. U.S. Pat. No. 4,615,226 - DiNuzzo et al. incorporated herein by reference discloses methods and apparatus for such automation. Automation also dramatically decreases the cost of analysis. Such automated injection devices are commercially available, for example, the HP 7673A, manufactured and sold by the Hewlett-Packard Corporation of Palo Alto, Calif.

Cool on-column injection still has unique advantages in relation to thermally labile or reactive compounds, very volatile compounds and/or wide boiling point mixtures. However, to fully utilize cool on-column injection as a technique, it must be robustly and reliably automatable. Current art limits cool on-column automation to capillary columns having inner diameters of 530 μ or larger, thereby greatly limiting the efficiency of the technique. Consequently, a need exists for an automated chromatographic apparatus and method which maximizes robustness and performance of cool on-column injections onto columns having inner diameters of less than 530 μ. It will be noted that a practical lower limit of cool on-column injection is approximately under 200 μ. This limit is dictated by the need for a syringe needle having a presently manufacturable wall thickness to also have an inner diameter large enough to permit liquid transfer into the inlet (approximately 100 μ minimum for most samples). A system that can address this 200–530 μ column inner diameter range can greatly broaden the applicability of the cool on-column technique.

SUMMARY OF THE INVENTION

The advantages of the invention are achieved in a system and method for performing cool, on-column sample injection into a chromatographic device having a capillary column which injection is achieved through the use of a syringe having a needle. The column length and diameter are minimized by the provision of an inlet assembly connected to the inlet end of the column, a sealing member disposed in the inlet assembly, for forming a fluid tight seal in the inlet end when the sample is injected onto the column to prevent the sample from escaping and for reducing the effective length of the needle at the point of insertion of the needle into the column and a temperature controller for controlling the temperature of the column in the region where the sample is injected in response to a first control signal. The sealing member may include an elastomeric member and further the system has included a mechanism for continuously cooling the elastomeric member. The elastomeric member is formed as a septum having a bore therein for passage of the needle therethrough. In such a system and method the need for a long syringe is obviated. The column inner diameter is minimized by the provision of apparatus which permits the needle of the syringe to have a minimum outer circumference.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENT

Figure 1:
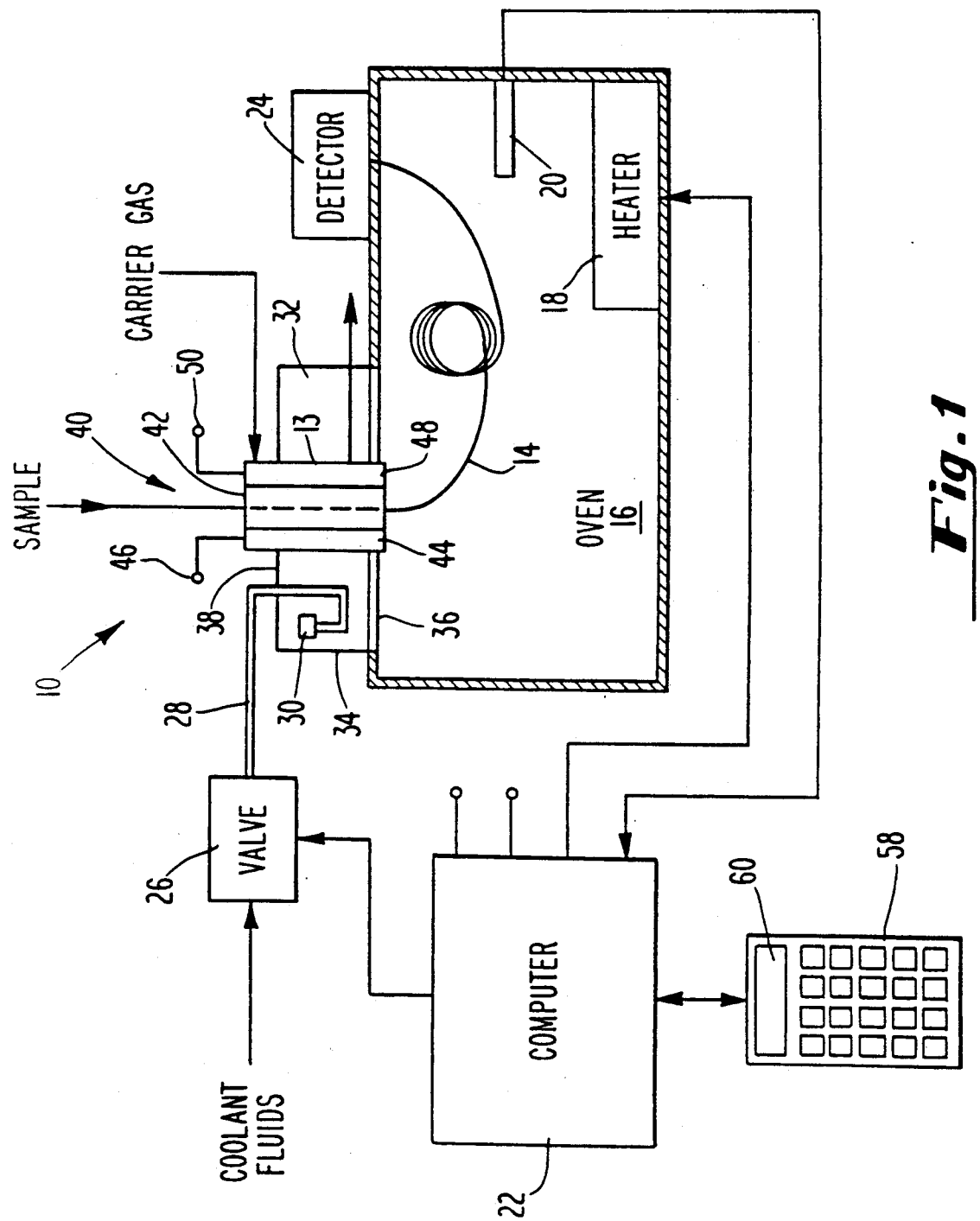
FIG. 1 is a block diagram of a gas chromatograph in which an automated cool, on-column system constructed in accordance with the present invention can be utilized.
Figure 2:
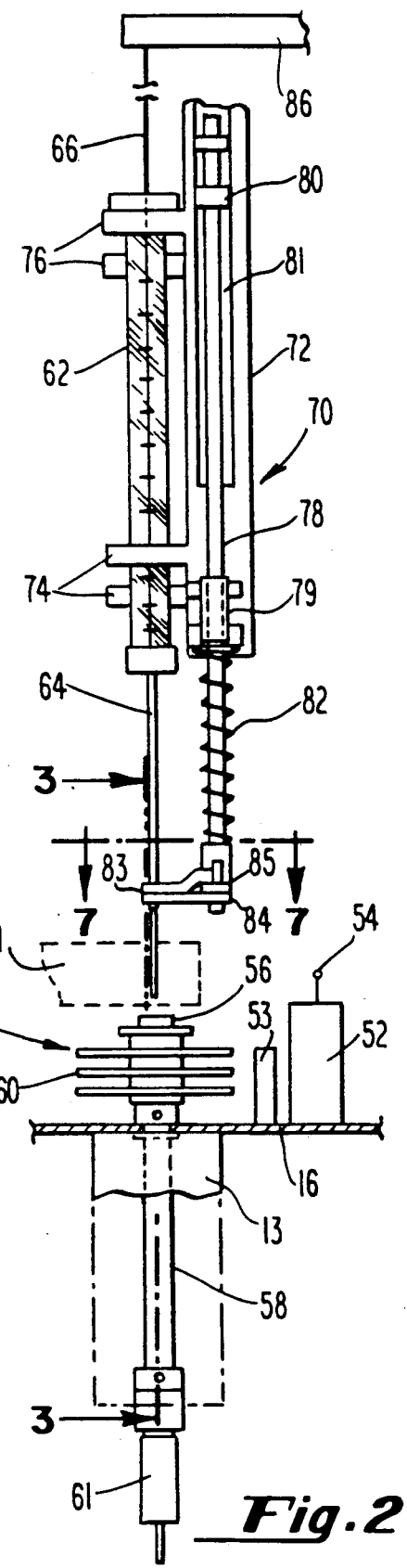
FIG. 2 is an elevational view of the automated cool, on-column system of the present invention.

A gas chromatograph (GC) is shown in FIG. 1 and is generally designated 10. In order to perform a chromatographic separation of a given sample compound, the sample is injected together with a pressurized carrier gas by means of injection port 12 (FIG. 2). The carrier gas supplied to injection port 12 is provided from a source through an appropriate valve (not shown), which serves to control the pressure of the carrier gas in the GC system. It will be noted at the outset that the present invention has overcome the major limitations of automated on-column injection directly onto narrow bore columns by replacing long slender needles susceptible to buckling with a short temperature transition zone in the inlet and with the reduction of the needle forces and effective length. The structure developed to achieve these results is shown in the drawings and is described hereinafter. Additionally it will be noted that, although the present invention is described in relation to a gas chromatography system, the applicability of the present invention is not so limited.

Column 14 is positioned within oven 16. Although no particular oven design is necessary in order to comply with the principles of the present invention, the oven should include a heating unit 18 and a temperature sensor 20. Heating unit 18 provides heat to oven 16 in response to a control signal generated by computer 22. In order to ensure that the temperature within the oven is at a desired level, sensor 20 generates a feedback signal representative of the temperature in oven 16, which signal is provided to computer 22. The carrier gas/sample combination passing through column 14 is exposed to a temperature per unit time profile resulting in part from the operation of heater 18 within oven 16. Typically, the temperature in oven 16 is increased from a minimum level to a maximum level in a linear or stepwise fashion. During this profile of changing temperatures, i.e., rising or falling, the sample will separate into its components primarily due to differences in the volatility characteristics of each component at a given temperature. As the components exit column 14 they are detected by detector 24. Detector 24 can be any of the known GC detectors such as a flame ionization detector or a mass spectrometer.

A portion of the temperature profile envisioned to be applied to column 14 in oven 16 will be below ambient or room temperature. The desired temperatures in this portion of the temperature profile are achieved through the use of a coolant fluid which is dispersed within oven 16. Coolant fluid of any appropriate type, such as liquid carbon dioxide or liquid nitrogen, is provided from a source not shown to valve 26. Valve 26 is open and closed in relation to the receipt of a control signal from computer 22. When valve 26 is open, the coolant fluid is passed through tube 28 and restrictor 30 into chromatograph 10. A shown in FIG. 1, the coolant fluid is deposited into an inlet chamber 32, which chamber is defined by inlet cover 34. Inlet cover 34 surrounds opening 36 in oven 16 so that fluid communication is established therebetween. As will be appreciated, coolant fluid exiting restrictor 30 will pass into chamber 32, through opening 36 and into oven 16. As shown in FIG. 1, restrictor 30 is directed so that coolant fluid exiting restrictor 30 is directed upwards towards the top wall 38 of cover 34. Coolant fluid passing through opening 36 serves to cool the interior of oven 16. Computer 22 controls the time during which valve 26 remains open in relation to the temperature sensed in oven 16 by sensor 20.

Inlet assembly 12 is shown diagrammatically in FIG. 1. Inlet 12 is preferably constructed as a block 13 of thermally conductive material. As will be described in greater detail in relation to FIGS. 2 and 3, the sample/carrier gas combination passes through central passage 42 and onto column 14. A cartridge heater 44 is provided for heating inlet assembly 40 in response to an actuation signal being provided at terminal 46. The temperature of inlet 12 is sensed by sensor 48 which generates an electrical signal representative of the temperature of inlet 12, which signal in turn is provided to terminal 50. Heater 44 in turn raises the temperature of inlet 12 to a desired level whereupon computer 22, based upon the signal from sensor 48, modifies the control signal supplied to terminal 46. Fan 52 serves to cool inlet 12 during the injection procedure by moving air across fins 53 and 60. An appropriate fan control signal is generated by computer 22 and provided to terminal 54. In the preferred embodiment, fan 52 is run continuously.

It will be noted that sensor 48 could be used by computer 22 in generating the control signal for valve 26. As coolant fluid is dispersed within chamber 32, the temperature of inlet 12 will also be modified. Any modifications to the temperature of inlet 12 will be sensed by sensor 48 and thus transmitted to computer 22 at terminal 50. In the preferred embodiment, valve 26 is controlled by the temperature sensed in the oven by sensor 20.

In the preferred embodiment, oven 16 is a Hewlett-Packard 5890A gas chromatograph. Such a gas chromatograph includes an internal fan, (not shown) which is more fully described in U.S. Pat. No. 4,181,613 Welsh, et al. which is incorporated herein by reference. The action of the fan in oven 16 will serve to drive a small portion of the coolant fluid through oven 16.

Referring to FIG. 1, the electronic controls are shown to include two main components, namely keypad 58, and computer 22. Computer 22 maintains overall control of all systems associated with gas chromatograph 10. It will be recognized that any particular gas chromatograph may include more systems than those described in relation to the present invention. It will also be understood that although computer 22 is shown as a single block, such computer includes a central processing unit and all associated peripheral devices, such as random access memories, read-only memories, input-/output isolation devices, clocks and other related electronic components. In the preferred embodiment, the central processor used in computer 22 is a Z80 microprocessor. As such, computer 22 includes a memory in which information and programming can be stored and retrieved by known methods. The programming associated with computer 22 which is utilized in relation to the present invention can be any programming sufficient to generate the necessary control signals to maintain the temperature at a desired level. Since the programming of computer 22 is simple, it will not be described in greater detail herein.

Two of the functions of computer 22 is the control of oven temperature and inlet temperature. Computer 22 controls oven temperature by transmitting an appropriate signal to heater 18 which causes heater 18 to increase or decrease the amount of heat transferred to oven 16 and/or by transmitting an appropriate signal to valve 26 which initiates or terminates the disbursement of coolant fluid within oven 16. Sensor 20 senses the temperature in oven 16 and transmits a feedback signal representative of such temperature to computer 22. By monitoring the temperature feedback signal from sensor 20 computer 22 can maintain the temperature in oven 16 at some desired level by controlling heater 18 and valve 26. Operating commands and other information are entered into computer 22 by way of keypad 58. Keypad 58 in the preferred embodiment is provided with a display screen 60. Consequently, indicating or prompt messages can be generated by computer 22 and displayed on keypad 58.

Computer 22 controls temperature of inlet 12 by transmitting an appropriate signal to heater 44 which causes heater 44 to increase or decrease the amount of heat transferred to block 40. Sensor 48 senses the temperature of block 40 and transmits a feedback signal representative such block temperature to computer 22. By monitoring the temperature feedback signal from sensor 48, computer 22 can maintain the temperature of inlet 12 at some desired level. Computer 22 in the preferred embodiment generates a control signal which is used to control valve 26, heater 18, and heater 44. Since the generated control signal will be in a digital form it is converted to analog form by a digital to analog converter (not shown) and appropriately amplified.

Referring now to FIG. 2, inlet 12 is shown in greater detail. Inlet 12 generally includes two axially aligned body portions 56 and 58, having a passage 59 (FIG. 3) formed therethrough. Upper body portion 56 has several fins 60 formed on its outer surface. As will be appreciated, inlet 12 is cooled by the movement of air across fin 60. Fan 52 is positioned to move air across fins 53 and 60. By such air movement, the septum located between body portions 56 and 58 is maintained cool. Column 14 passes through the outlet end of bottom body portion 58 and is held in place by connector 61.

In the preferred embodiment of the present invention, cool on-column injections are made using a syringe 62. Syringe 62 is shown to include a needle 64 and a plunger 66. It will be appreciated that as plunger 66 is pulled from syringe 62, samples can be drawn into syringe 62 through needle 64. Conversely, as plunger 66 is pushed into syringe 62, any sample contained therein will be ejected from needle 64.

The objective in cool, on-column injections is to insert the tip of needle 64 into column 14 so that when plunger 66 is moved the sample is ejected directly onto column 14. To this end, a positioning mechanism, generally designated 70, is provided for positioning syringe 62 at the opening of inlet 12 and for moving syringe 62 axially with respect to column 14 s that needle 64 is inserted into column 14.

Positioning mechanism 70 is shown to include a base member 72 which is capable of axial movement in relation to said inlet assembly. Such axial movement can be achieved by any known means, for example, a robot manipulator arm or to a frame having an arrangement of motors and pulleys similar to that shown in U.S. Pat. No. 4,615,226 incorporated herein by reference or that contained in the HP 7673A device described above. Two opposed pairs of fingers 74 and 76 are attached to base member 72 and serve to hold syringe 62 in a fixed position relative to base 72. As will be appreciated, axial movement of base 72 will result in the axial movement of syringe 62.

A rod 78 is slidingly attached to base 72 in a fashion which permits axial movement in relation to movement of base 72. Rod 78 is attached to base 72 via collar 79 and bracket 80. While collar 79 is fixed in relation to base 72, bracket 80 slides within slot 81. Spring 82 serves to maintain rod 78 in the normally extended position shown in FIG. 2. Such extended position is achieved by fixing one end of spring 82 to base 72 by any suitable means and by placing the other end against the needle grasping member 83 securely attached to the end of rod 78. As will be described in greater detail in relation to FIGS. 7 and 9, grasping member 83 includes a pair of arms 84 and 85 which are capable of pinching movement relative to one another so that needle 64 is held when arms 84 and 85 are pinched together. The pinching movement is achieved by fixedly mounting arm 84 to rod 78 and by pivotally mounting arm 85 to rod 78. The pivoting movement cf arm 85 creates a pinching movement between arms 84 and 85.

Arm 86 is attached to plunger 66 and serves to move plunger 66 into or out of cylinder 62. Although not shown, arm 86 can be attached to any suitable movement mechanism capable of providing axial movement of plunger 66. Such a mechanism is contained in U.S. Pat. No. 4,615,226 or that contained in the HP 7673A device described above.

Figure 3:
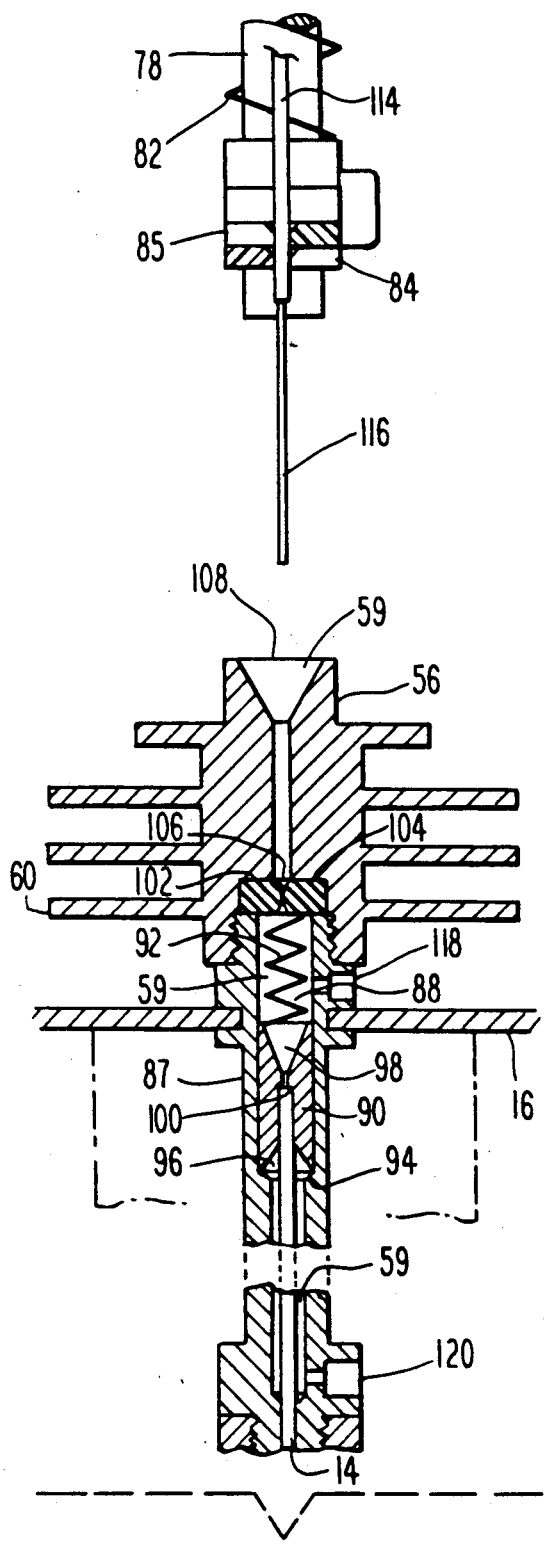
FIG. 3 is a section view along the line 3—3 of FIG. 2.

Referring now to FIG. 3, body portions 56 and 58 are identified in greater detail. Body portion 58 is shown to include an outer cylindrical portion 87 defining a central bore 88 and an insert portion 90 which is capable of axial movement within bore 88. It will be noted that bore 88 forms a portion of passage 59. Insert 90 is biased by spring 92 against shoulder 94. Insert 90, and thus body portion 58, is provided with an outlet end 96 for connection with column 14 and a frusto-conically shaped inlet end 98. As will be appreciated, when column 14 is inserted into body portion 58, the user cannot see movement of the column. Spring 92 provides a tactile indication that the column has been fully inserted due to the end of column 14 coming to rest on shoulder 100 of insert 90. Thereafter continued insertion of column 14 by the user will result in movement of insert 90 against spring 92. Spring 92 will require the user to exert greater force to continue inserting column 14.

Outlet end 96 of insert 90 is also shown to include a frusto-conical shape which assists in guiding column 14 during insertion. A cylindrical cavity 102 is formed at the outlet end of upper body member 56. The inlet end of outer cylinder portion 87 is formed to threadingly engage body portion 56 within cavity 102. Positioned between the bottom of cavity 102 and the top of outer cylinder 87 is septum 104. Septum 104 acts as a sealing member for sealing the central passage through inlet 12. To this end, septum 104 is formed from an elastomeric material and has a central orifice 106 passing therethrough. As shown in FIG. 3, a pre-load force has been applied to septum 104, deforming the septum slightly in orifice 106 closing central passage 59. The degree of threaded engagement between body portions 56 and 58 will determine the amount of pre-load force. The importance of the dimensions of orifice 106 will be explained in greater detail hereinafter. Upper body portion 56 is provided with a frusto-conically shaped inlet 108 for guiding needle 64 into passage 59.

As shown in FIG. 3, needle 64 is a tapered needle having a base portion 114 and an end portion 116. Base portion 114 is of a first circumference and end portion 116 is of a second smaller circumference. The outer diameter of end portion 116 is less than the inner diameter of column 14. By providing the tapered structure to needle 64, end portion 116 can have a minimum outer circumference while maximizing its resistance to bending and buckling. Resistance of the isolated needle to buckling has been maximized by reducing to a minimum the length of needle of narrowest diameter. As will be appreciated from the Euler formula, such a reduction in length significantly increases the force required to buckle the needle.

The diameter of orifice 106 in septum 104 in sufficiently wide and the pre-load force is such that end portion 116 passes therethrough with a force below that which would buckle the needle. The engagement by base portion 114 of the walls of orifice 106 provides additional support to end portion 116 and acts to reduce the effective length of portion 116. Such reduction in effective length results in an increase in the force required to buckle needle end portion 116 during insertion into column 14.

Lower body portion 58 is shown to include an inlet opening 120 and an outlet opening 118 for passage of the carrier gas. As will be appreciated, when end portion 116 is inserted into column 14 carrier gas passing through opening 120 Will pass around end portion 116 and into column 14. Gas not passing into column 14 will pass out of body portion 58 through outlet 118.

Consider now the system of the present invention for performing a cool, on-column injection of the sample into gas chromatograph 10. The low thermal mass inlet assembly 12, the cooling of the inlet assembly, including the septum, and the relatively short temperature transition zone resulting from the inlet assembly structure described above, allows the use of a relatively short needle 64 for on-column injection. It will be recalled, that previously, relatively long needles were used for such injections.

Figure 6:
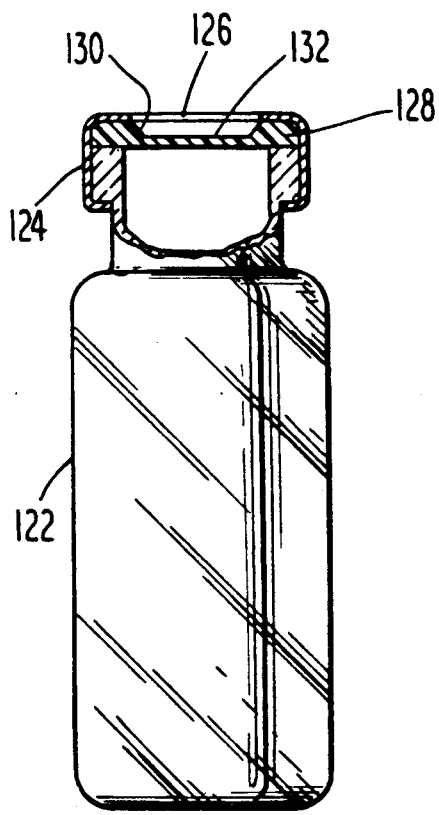
FIG. 6 is a sample container having a vial cap constructed in accordance with the present invention.

Initially, it will be necessary to place a sample into syringe 62. Since end portion 116 will be the inlet to cylinder 62 during sample acquisition, it is necessary that the forces acting on end portion 116 be minimized during such acquisition procedure. In accordance with the present invention, a new and novel vial has been developed which is shown in FIG. 6. Vial 122 is shown to include closure 124 having a central opening 126. Closure 124 holds pierceable stopper or vial cap 128 over the opening of vial 122. It will be noted that pierceable stopper 128 is formed from a material selected from the group consisting of silicone rubber, polytetrafluoroethylene faced silicone rubber and fluorocarbon rubber. Stopper 128 is shown to include a support portion 130 of a first thickness and a piercing portion 132 of a second smaller thickness. The structure of stopper 128 allows for minimal piercing forces in order to remove sample contained within vial 122.

During operation of gas chromatograph 10, a positioning mechanism moves member 70 and thus syringe 62 so that needle 64 is generally axially aligned with vial 122. In the preferred embodiment, except for the structure shown in FIGS. 3-9, the positioning mechanism is identical to that contained in the HP 7673A automatic injector, referred to above. Consequently, in the preferred embodiment, vial 122 is moved into alignment with syringe 62 by the rotation of turret 121. Base 72 is moved axially towards vial 122 resulting in needle 64 piercing stopper 128 in the region of piercing portion 132. Arm 86 then moves pulling plunger 66 axially out of syringe 62 drawing sample from vial 122 into syringe 62. When a desired amount of sample has been acquired, base member 72 pulls needle 64 from vial 122. Turret 121 is thereafter rotated moving vial 122 clear of needle 64. Rotation of turret 121 continues until a throughbore is aligned with needle 64, so that syringe 62 and needle 64 are now positioned over the opening to inlet 12 which is generally shown in FIG. 3.

Figure 4:
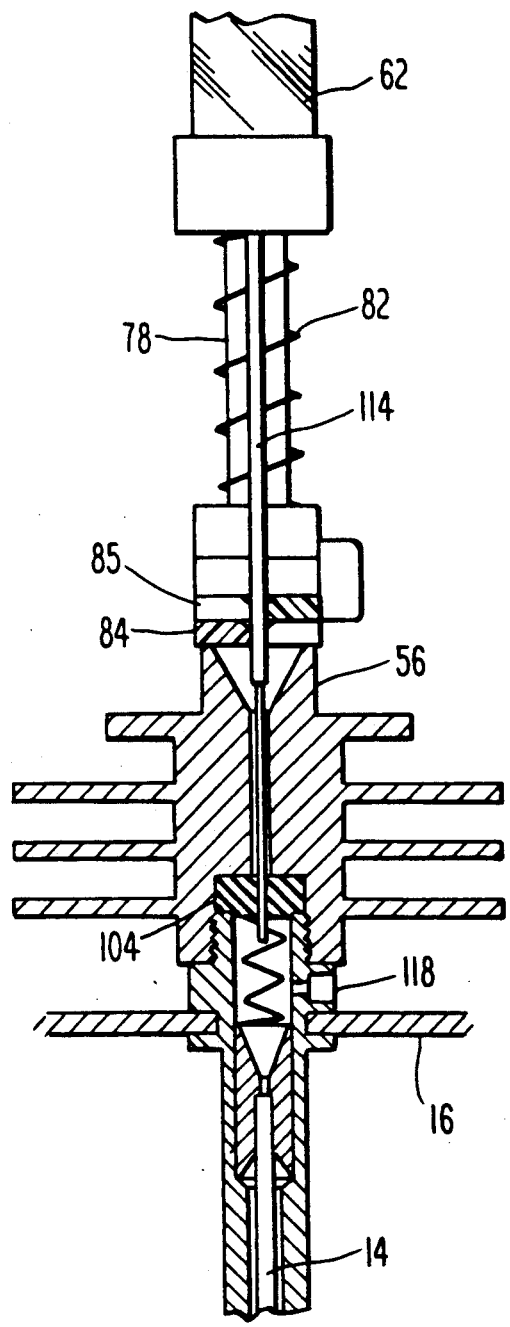
FIG. 4 is a section view of the apparatus shown in FIG. 3, wherein the needle has been fully lowered in the holder.

Once cylinder 62 is positioned over the opening to inlet 12, base 72 moves axially until arm 84 is stopped by upper body portion 56. Such position is shown in FIG. 4. When syringe 62 is moved into this position, end portion 116 passes through upper body portion 56 and orifice 106. It should be noted that while end portion 116 is being forced through closed orifice 106 in septum 104, that arms 84 and 85 serve to support needle 64 reducing the effective length.

Figure 5:
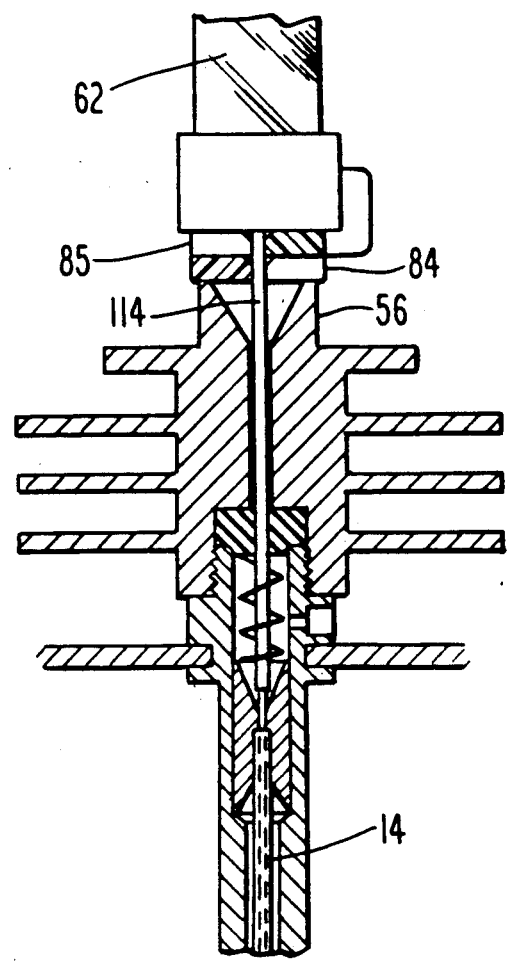
FIG. 5 is a section view of the apparatus shown in FIG. 3, wherein the needle has been fully lowered in the inlet.

As shown in FIG. 5, base 72 has been lowered so that spring 82 has been fully compressed and syringe 62 has nearly made contact with arm 85. As syringe 62 moves into the position shown in FIG. 5, base portion 114 engages septum 104 resulting in a shortening of the needle effective length, i.e. end portion 116 is reinforced such that the force required to buckle end portion 116 is increased. End portion 116 of needle 64 moves through the inlet end of insert 90 and into column 14. By movement of arm 86, the sample contained within syringe 62 is injected onto column 14.

Figure 8:
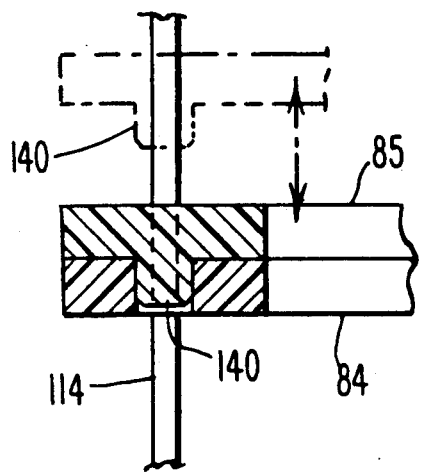
FIG. 8 is a section view along the line 8—8 of FIG. 7.
Figure 7:
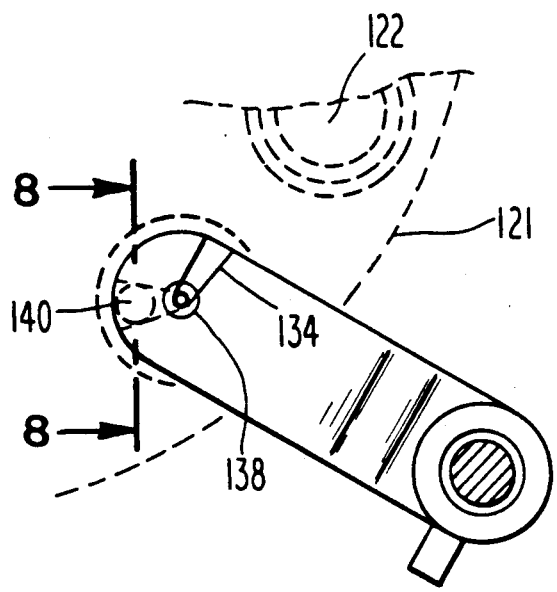
FIG. 7 is a section view along the line 7—7 of FIG. 2.
Figure 9:
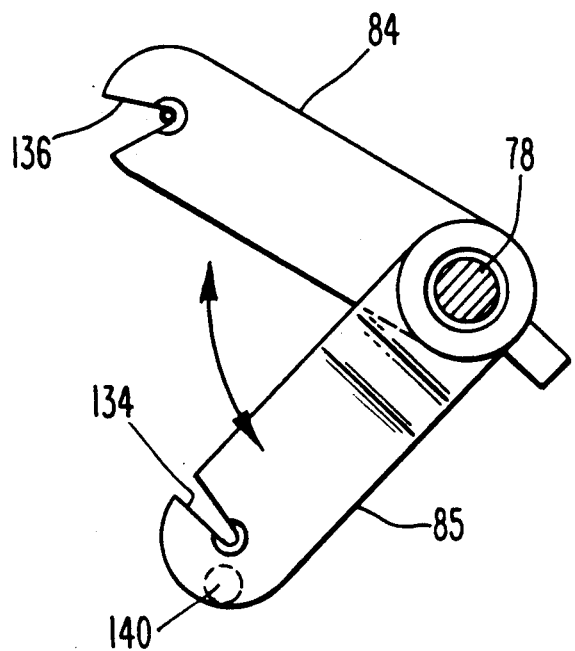
FIG. 9 is an alternative view of FIG. 7, wherein the arms are depicted in an open position.

Consider now the more detailed description of arms 84 and 85 shown in FIGS. 7-9. As indicated previously, arms 84 and 85 are attached to rod 78 such that pivotal movement of arm 85 results in a pinching of needle 64. As shown in FIG. 9, arms 84 and 85 are provided with slots 136 and 134 respectively. The slots are shaped so that when arms 84 and 85 are brought together a portion of each slot overlays forming a bore 138. During operation, needle 64 is supported continuously by bore 138. As shown in FIG. 8, arm 85 includes a projection 140. Projection 140 serves to lock arms 84 and 85 together by its positioning or extension into slot 136. The pivotal sliding attachment of arm 85 to rod 78 allows arm 85 to be lifted and lowered in relation to arm 84 in order to position projection 140 in slot 136.

Finally, in the preferred embodiment it will be noted that septum 104 has a thickness of approximately 3.20 mm prior to pre-loading and a thickness of approximately 2.05 mm after preloading, resulting in a compression of 1.15 mm, plus or minus 0.18 mm. Also in the preferred embodiment orifice 106 has an inner diameter of approximately 0.45 mm prior to loading. End portion 116 has a preferred outer diameter of approximately 0.2286 mm and base portion 114 has a preferred outer diameter of approximately 0.4572 mm.

In the preferred embodiment, there is a smooth gradual transition in diameter from end portion 116 to base portion 114 to maximize stress concentration at the transition point where buckling is most likely to occur. In this preferred embodiment, automated cool on-column injection directly onto 320 $\mu$ inner diameter capillary columns is made possible.

While the invention has been described and illustrated with reference to specific embodiments, those skilled in the art will recognize that modification and variations may be made without departing from the principles of the invention as described herein above and set forth in the following claims.

What is claimed is:

1. A method for performing cool, on-column sample injection into a chromatographic device having a capillary column having an inlet end, said method comprising the steps of:
   providing a syringe incorporating a needle having an effective length through which injection onto said column is achieved by insertion of said effective length into said column;
   providing an inlet assembly connected to said inlet end of said column;
   forming a low pierce force fluid tight seal in said inlet end when said sample is injected onto said column to prevent said sample from escaping from said column and reducing said effective length of said needle at the point of insertion of said needle into said column;
   supporting said needle during insertion into said column, thereby reducing said effective length.

2. The method of claim 1 further comprising the step of controlling the temperature of said column in relation to the boiling point of said sample in the region where said sample is injected, so that the length of the inlet assembly through which said needle passes and the effective length of said needle required for on-column injection are minimized.

3. The method of claim 1, wherein said inlet assembly comprises an inlet body having fins formed on the outer surface thereof and further comprising the step of cooling said inlet assembly by moving air across said fins.

4. The method of claim 1, wherein said step of sealing said inlet comprises positioning a septum in said inlet assembly and further comprising the step of applying a pre-load force to said septum, wherein said septum is formed from elastomeric material having a central orifice formed therethrough and wherein said step of applying a pre-load force comprises compressing said septum.

5. A system of performing cool, on-column sample injection into a chromatographic device having a capillary column having an inlet end through which injection is achieved through the use of a syringe having a needle, said system comprising:
   an inlet assembly connected to said inlet end of said column;
   a low pierce force seal, disposed in said inlet assembly, for forming a fluid tight seal in said inlet end when said sample is injected onto said column to prevent said sample from escaping from said column and for reducing the effective length of said needle at the point of insertion of said needle into said column; and
   temperature means for controlling the temperature of said column in relation to the boiling point of said sample in the region where the sample is injected, so that the length of the inlet assembly through which said needle passes and the effective length of said needle required for on-column injection are minimized.

6. The system of claim 5, wherein said low pierce force seal comprises an elastomeric member defining a septum having a bore formed therein for passage of said needle therethrough and further comprising cooling means for actively cooling said elastomeric member in said inlet assembly, so as to maintain seal integrity and minimize thermal degradation.

7. A system for performing cool, on-column sample injection into a chromatographic device having a capillary column having an inlet end, said system comprising:
   a syringe incorporating a needle having an effective length through which injection onto said column is achieved by insertion of said effective length into said column;
   an inlet assembly connected to said inlet end of said column;
   sealing means, disposed in said inlet assembly, for forming a fluid tight seal in said inlet end when said sample is injected onto said column to prevent said sample from escaping from said column and for reducing said effective length of said needle at the point of insertion of said needle into said column, wherein said sealing means is pierced by said effective length with a minimum force; and
   guide means, for reducing said effective length and for supporting said needle during insertion into said column.

8. The system of claim 7, further comprising temperature means for controlling the temperature of said column in relation to the boiling point of said sample in the region where the sample is injected, so that the length of the inlet assembly through which said needle passes and the effective length of said needle required for on-column injection are minimized.

9. The system of claim 7, wherein said inlet assembly comprises an inlet body having fins formed on the outer surface thereof, said inlet assembly having a low mass and being formed from aluminum, and further comprising a fan positioned to move air across said fins for actively cooling said sealing means.

10. The system of claim 7, wherein said inlet assembly comprises first and second axially aligned body portions having a passage formed therethrough, and wherein said sealing means is positioned between said first and second body portions for sealing said passage around said needle.

11. The system of claim 10, wherein said sealing means comprises a septum formed from elastomeric material having a central orifice formed therethrough, said inlet assembly further comprising threaded members attached to each of said first and second body portions for threadingly joining said body portions together, so that said septum is secured therebetween and a preload force is applied to said septum, whereby upon application of said pre-load force said orifice closes, the amount of pre-load force applied to said septum being determined by the degree of threaded engagement between said body portions.

12. The system of claim 7, further comprising automated positioning means for mechanically positioning said syringe at the opening of said inlet assembly and for moving said syringe axially with respect to said column so that said needle is inserted into said column, whereby said needle maintains axial alignment with said column such axial movement.

13. The system of claim 12, wherein said guide means comprises:
   a rod slidingly attached to said automated positioning means in a fashion which permits axial movement of said rod in relation to the movement of said automated positioning means;
   a spring for biasing one end of said rod in an axially extended position; and
   grasping means, attached to the extended end of said rod, for grasping said needle, so that when said base is moved towards said inlet end said grasping means contacts said inlet assembly resulting in the axial retraction of said rod and the provision of continuous support to said needle.

14. The system of claim 13, wherein said grasping means comprises a pair of arms capable of pinching movement relative to one another and having opposed slots formed through each so that when said arms are brought together, said needle is held within each of said slots.

15. The system of claim 14, further comprising a projection formed on one of said arms and located so that when said arms are brought together said projection extends into the slot formed on the other arm and serves to hold the arms together.

16. The system of claim 15, wherein said slots are shaped so that when said arms are brought together a portion of each of said slots overlays one another to form a bore through which said needle passes.

17. The system of claim 7, wherein said needle comprises a base portion of a first circumference and an end portion of a second circumference, wherein said end portion is smaller than said base portion.

18. The system of claim 17, wherein said needle further comprises a smooth gradual transition portion between said first circumference and said second circumference.

19. The system of claim 18, wherein said sealing means comprises a septum formed from elastomeric material having a central orifice formed therethrough, and wherein said inlet assembly applies a pre-load force to said septum, said pre-load force being such that said end portion of said needle can pass through said septum with minimum force and wherein said orifice closes around said base portion, whereby said sealing means reduces the effective length of said needle at the point of insertion of said needle into said column by engaging said base portion of said needle.

20. The system of claim 19, wherein the circumference of said base portion is equal to the inner circumference of said central orifice.

21. The system of claim 20, further comprising a vial, from which said sample is obtained, a vial cap and attachment means for attaching said vial cap to said vial, wherein said vial cap comprises a support portion of a first thickness and a piercing portion of a second thickness, wherein as said needle passes through said piercing portion to obtain said sample a low level axial force is applied to said needle.

22. The system of claim 21, wherein said vial cap is formed from a material selected from the group consisting of silicone rubber, polytetrafluoroethylene faced silicone rubber and fluorocarbon rubber.

* * * * *